(12) United States Patent
Eichholz et al.

(10) Patent No.: US 12,157,696 B2
(45) Date of Patent: Dec. 3, 2024

(54) METHOD FOR HEATING MOLTEN GLASS AND GLASS ARTICLE

(71) Applicant: SCHOTT AG, Mainz (DE)

(72) Inventors: Rainer Erwin Eichholz, Frankfurt am Main (DE); Josef Rasp, Waldsassen (DE); Michael Hahn, Hohenstein (DE); Stefan Knoche, Mainz (DE)

(73) Assignee: Schott AG, Mainz (DE)

( * ) Notice: Subject to any disclaimer, the term of this patent is extended or adjusted under 35 U.S.C. 154(b) by 159 days.

(21) Appl. No.: 17/748,393

(22) Filed: May 19, 2022

(65) Prior Publication Data

US 2022/0274862 A1 Sep. 1, 2022

Related U.S. Application Data

(63) Continuation of application No. PCT/EP2020/082962, filed on Nov. 20, 2020.

(30) Foreign Application Priority Data

Nov. 21, 2019 (DE) .................... 10 2019 217 977.0

(51) Int. Cl.
| | | |
|---|---|---|
| C03C 3/078 | (2006.01) | |
| C03B 5/03 | (2006.01) | |
| C03B 5/167 | (2006.01) | |
| C03B 5/225 | (2006.01) | |
| C03C 3/083 | (2006.01) | |

(Continued)

(52) U.S. Cl.
CPC ................ *C03C 3/078* (2013.01); *C03B 5/03* (2013.01); *C03B 5/1672* (2013.01); *C03B 5/225* (2013.01); *C03C 3/083* (2013.01); *C03C 3/087* (2013.01); *C03C 3/089* (2013.01); *C03C 3/091* (2013.01); *C03C 3/093* (2013.01); *C03B 5/027* (2013.01); *C03C 2201/10* (2013.01); *C03C 2201/32* (2013.01); *C03C 2201/50* (2013.01);

(Continued)

(58) Field of Classification Search
CPC .............. C03B 5/03; C03B 5/027–031; C03C 2203/10; G01N 21/59; G01N 33/386
See application file for complete search history.

(56) References Cited

U.S. PATENT DOCUMENTS

| | | |
|---|---|---|
| 6,465,381 B1 | 10/2002 | Lautenschläger et al. |
| 7,087,669 B2 | 8/2006 | Ota et al. |

(Continued)

FOREIGN PATENT DOCUMENTS

| | | |
|---|---|---|
| JP | 5-97443 A | 4/1993 |
| JP | 2009-523697 A | 6/2009 |

(Continued)

OTHER PUBLICATIONS

International Search Report dated Apr. 9, 2021 for International Application No. PCT/EP2020/082962 (4 pages).

(Continued)

*Primary Examiner* — Jasper Saberi
(74) *Attorney, Agent, or Firm* — Taylor IP, P.C.

(57) ABSTRACT

A glass article is designed at least in part in the form of a glass tube element including at least one shell which encloses at least one lumen. For at least one light transmission analysis of the glass article, a ratio of an average amplitude transmission factor and a specific amplitude transmission factor is greater than 1.00001.

18 Claims, 4 Drawing Sheets

(51) Int. Cl.
*C03C 3/087* (2006.01)
*C03C 3/089* (2006.01)
*C03C 3/091* (2006.01)
*C03C 3/093* (2006.01)
C03B 5/027 (2006.01)
G01N 21/59 (2006.01)
G01N 33/38 (2006.01)

(52) U.S. Cl.
CPC ...... *C03C 2201/54* (2013.01); *C03C 2203/10* (2013.01); *G01N 21/59* (2013.01); *G01N 33/386* (2013.01)

(56) References Cited

U.S. PATENT DOCUMENTS

| | | | |
|---|---|---|---|
| 9,802,850 B2 | 10/2017 | Ohmstede et al. | |
| 10,358,371 B2 | 7/2019 | Duch et al. | |
| 11,028,001 B2 | 6/2021 | De Angelis et al. | |
| 2003/0159465 A1 | 8/2003 | Bowden et al. | |
| 2006/0144089 A1* | 7/2006 | Eichholz | C03B 5/235 65/29.21 |
| 2010/0218558 A1* | 9/2010 | Gross | C03B 5/03 65/135.6 |
| 2017/0305775 A1 | 10/2017 | Duch et al. | |
| 2019/0308899 A1 | 10/2019 | Schmitt et al. | |

FOREIGN PATENT DOCUMENTS

| | | | |
|---|---|---|---|
| JP | 2016-188147 A | 11/2016 | |
| WO | WO-2018204549 A1 * | 11/2018 | C03B 5/027 |

OTHER PUBLICATIONS

German Office Action dated Jun. 5, 2020 for German Application No. 10 2019 217 977.0 (8 pages).

* cited by examiner

METHOD FOR HEATING MOLTEN GLASS AND GLASS ARTICLE

CROSS REFERENCE TO RELATED APPLICATIONS

The present application is a continuation of International Patent Application No. PCT/EP2020/082962, filed on Nov. 20, 2020, which is herein incorporated by reference. International Patent Application No. PCT/EP2020/082962 claims priority to German Patent Application No. DE 10 2019 217 977.0 filed on Nov. 21, 2019, which is herein incorporated by reference.

BACKGROUND OF THE INVENTION

1. Field of the Invention

The present disclosure relates to a method for heating molten glass. The disclosure also relates to a glass article.

2. Description of the Related Art

In the state of the art glass is melted and heated in a glass melting furnace. For this purpose often the glass is melted by hot gases from flames provided across the furnace above the glass surface. For heating the molten glass usually an electric current is passed through the bath of molten glass between electrodes immersed in the molten glass. Materials of the electrodes are typically chosen from molybdenum (Mo), tungsten (W) or noble metals such as Platinum (Pt), Rhodium (Rh) and Iridium (Ir).

However, such electrodes are subject to corrosion and removal of electrode material during use. Respective particles emanating from the electrodes can then also be found in the molten glass material. This in turn leads to contaminations of the final glass articles produced from the molten glass.

Such contaminations may manifest themselves in accumulations of small particles or striae of respective materials or a combination thereof in the glass material.

Thus, for obtaining glass articles with reduced or even no such contaminations, so far glass material which can be molten with technologies such as microwave heating had to be used.

SUMMARY OF THE INVENTION

It is, thus, an object of the present disclosure to overcome the disadvantages described above with respect to the state of the art by providing ways which allow a reduction of the contaminations in the glass material produced in glass melting furnaces. It is further the object of the present disclosure to provide glass articles of high quality.

These and other objects are addressed in the present disclosure. The objects are in particular solved by the disclosure according to a first aspect in that a method for heating molten glass is provided, the method comprising the steps:

Providing two or more electrodes and bringing each of them at least in part in contact with the molten glass;
Applying a voltage between a first electrode and a second electrode, with the voltage being an AC voltage; and
Controlling the temperature of the molten glass, which comprises one or more of the following steps:

i. Controlling the frequency of the applied voltage such that it is between 30 Hz and 15 kHz; and
ii. Controlling the specific current load at the first and/or second electrode, such that it is 3.0 A/cm$^2$ or less at the surface of the electrode which has contact with the molten glass.

The object is solved by the disclosure according to a second aspect in that a glass article, the glass article being designed at least in part in form of a glass tube element comprising at least one shell which encloses at least one lumen, wherein for at least one light transmission analysis of the glass article, the ratio of an average amplitude transmission factor and a specific amplitude transmission factor is greater than 1.00001, wherein for the light transmission analysis, the outer surface of the shell is at least virtually divided into surface areas of equal shape and size, and an amplitude transmission factor of a light beam, which is emitted from a fixed light source towards a fixed detector along a beam path, is determined consecutively for every surface area in that the glass article and/or the surface area is positioned relative to the beam path such that the light beam propagates through the thickness of the shell and crosses the respective surface area perpendicularly, wherein the amplitude transmission factors of all surface areas are arranged within a sorted list from small values to large values, wherein the specific amplitude transmission factor is the mean value of the first 1% of the amplitude transmission factors arranged in the sorted list, the smallest one being among the first 1% of the amplitude transmission factors, wherein the average amplitude transmission factor is the mean value of all amplitude transmission factors arranged in the sorted list, wherein in certain embodiments:
(i) the specific amplitude transmission factor is smaller than or equal to 0.9999, smaller than or equal to 0.9995, smaller than or equal to 0.999 or smaller than or equal to 0.995, such as between 0.99 and 0.995, such as between 0.99 and 0.999;
(ii) the average amplitude transmission factor is larger than or equal to 0.99, larger than or equal to 0.993, larger than or equal to 0.996, such as between 0.996 and 1.0, such as between 0.996 and 0.999, larger than or equal to 0.999, larger than or equal to 0.9995, or larger than or equal to 0.9999;
(iii) the ratio is greater than 1.00003, greater than 1.00005, greater than 1.0001, greater than 1.0003, greater than 1.0005, greater than 1.001, greater than 1.003, greater than 1.005, greater than 1.01, greater than 1.03, greater than 1.05 or greater than 1.1;
(iv) the amplitude transmission factor is the factor the amplitude of the light beam is attenuated between the light source and the detector;
(v) wherein the amplitude transmission factors of all surface areas are individually corrected so as to be independent from the distance, the light beam propagates for the respective surface area through the glass material of the shell thickness of the glass article;
(vi) the light beam has a wavelength of between 270 nm and 300 nm, such as of between 275 nm and 290 nm;
(vii) the light source comprises a laser;
(viii) the light beam has an amplitude of 10 Volts per meter or less at the light source;
(ix) the outer surface of the shell is divided in 10 or more, 100 or more, 500 or more, 1000 or more, 3000 or more, 5000 or more or 10000 or more equal surface areas;

(x) each surface area has a first extension of between 0.5 mm and 2.5 mm, such as of between 1.0 mm and 2.0 mm and/or a second extension of between 0.5 mm and 2.5 mm, such as of between 1.0 mm and 2.0 mm, such as the first and second extensions are equal; and/or (xi) for measuring the amplitude transmission factors, the glass article is divided into two or more parts, such as into two or four parts such that each cutting plane comprises the center axis of the shell.

In accordance with an aspect of the disclosed subject matter, a glass article is provided. The glass article being designed at least in part in form of a glass tube element comprising at least one shell which encloses at least one lumen, wherein for at least one light transmission analysis of the glass article, the ratio of an average amplitude transmission factor and a specific amplitude transmission factor is greater than 1.00001, wherein for the light transmission analysis, an outer surface of the shell is at least virtually divided into surface areas of equal shape and size, and an amplitude transmission factor of a light beam, which is emitted from a fixed light source towards a fixed detector along a beam path, is determined consecutively for every surface area in that the glass article and/or the surface area is positioned relative to the beam path such that the light beam propagates through the thickness of the shell and crosses the respective surface area perpendicularly, wherein the amplitude transmission factors of all surface areas are arranged within a sorted list from small values to large values, wherein the specific amplitude transmission factor is the mean value of the first 1% of the amplitude transmission factors arranged in the sorted list, the smallest one being among the first 1% of the amplitude transmission factors, wherein the average amplitude transmission factor is the mean value of all amplitude transmission factors arranged in the sorted list, wherein the average amplitude transmission factor is larger than or equal to 0.99; wherein the amplitude transmission factor is the factor the amplitude of the light beam is attenuated between the light source and the detector; wherein the light beam has a wavelength of between 270 nm and 300 nm; wherein the light source comprises a laser; and wherein the outer surface of the shell is divided in 10 or more equal surface areas.

In certain illustrative embodiments, the average amplitude transmission factor is larger or equal to 0.993.

In certain illustrative embodiments, the shell has an overall average concentration of molybdenum, platinum, iridium, tungsten, rhodium, noble metals, alloys of one or more of these materials or oxides of one or more of these materials, respectively, of at least 0.1 ppm (m/m) but less than 50 ppm (m/m).

In certain illustrative embodiments, the specific amplitude transmission factor is smaller than or equal to 0.9999.

In certain illustrative embodiments, the ratio is greater than 1.00003.

In certain illustrative embodiments, the glass article has a length of between 1 m and 3 m.

In certain illustrative embodiments, the glass element comprises in weight percent:

| | |
|---|---|
| $SiO_2$ | 50-90 |
| $B_2O_3$ | 0-20 |
| $Al_2O_3$ | >0-18 |
| $Na_2O$ | 0-15 |
| $K_2O$ | 0-5 |
| $Li_2O$ | 0-2 |
| CaO | 0-15 |
| BaO | 0-6 |
| $ZrO_2$ | 0-5 |
| $TiO_2$ | 0-5 |
| $Fe_2O_3$ | 0-3 |

In accordance with an aspect of the disclosed subject matter, a glass article is provided. The glass article being designed at least in part in form of a glass tube element comprising at least one shell which encloses at least one lumen, wherein for at least one light transmission analysis of the glass article, the ratio of an average amplitude transmission factor and a specific amplitude transmission factor is greater than 1.00003, wherein for the light transmission analysis, the outer surface of the shell is at least virtually divided into surface areas of equal shape and size, and an amplitude transmission factor of a light beam, which is emitted from a fixed light source towards a fixed detector along a beam path, is determined consecutively for every surface area in that the glass article and/or the surface area is positioned relative to the beam path such that the light beam propagates through the thickness of the shell and crosses the respective surface area perpendicularly, wherein the amplitude transmission factors of all surface areas are arranged within a sorted list from small values to large values, wherein the specific amplitude transmission factor is the mean value of the first 1% of the amplitude transmission factors arranged in the sorted list, the smallest one being among the first 1% of the amplitude transmission factors, wherein the average amplitude transmission factor is the mean value of all amplitude transmission factors arranged in the sorted list; wherein the shell has an overall average concentration of molybdenum, platinum, iridium, tungsten, rhodium, noble metals, alloys of one or more of these materials or oxides of one or more of these materials, respectively, of at least 0.1 ppm (m/m) but less than 50 ppm (m/m); wherein the amplitude transmission factor is the factor the amplitude of the light beam is attenuated between the light source and the detector; wherein the light beam has a wavelength of between 270 nm and 300 nm; wherein the light source comprises a laser; and wherein the outer surface of the shell is divided in 10 or more equal surface areas.

In certain illustrative embodiments, the specific amplitude transmission factor is smaller than or equal to 0.9999.

In certain illustrative embodiments, the ratio is greater than 1.00003.

In certain illustrative embodiments, the glass article has a length of between 1 m and 3 m.

In certain illustrative embodiments, the glass element comprises in weight percent:

| | |
|---|---|
| $SiO_2$ | 50-90 |
| $B_2O_3$ | 0-20 |
| $Al_2O_3$ | >0-18 |
| $Na_2O$ | 0-15 |
| $K_2O$ | 0-5 |
| $Li_2O$ | 0-2 |
| CaO | 0-15 |
| BaO | 0-6 |
| $ZrO_2$ | 0-5 |
| $TiO_2$ | 0-5 |
| $Fe_2O_3$ | 0-3 |

In accordance with an aspect of the disclosed subject matter, a glass article is provided. The glass article being designed at least in part in form of a glass tube element comprising at least one shell which encloses at least one lumen, wherein for at least one light transmission analysis of the glass article, the ratio of an average amplitude transmission factor and a specific amplitude transmission factor is greater than 1.00001, wherein for the light transmission analysis, the outer surface of the shell is at least virtually divided into surface areas of equal shape and size, and an amplitude transmission factor of a light beam, which is emitted from a fixed light source towards a fixed detector along a beam path, is determined consecutively for every surface area in that the glass article and/or the surface area is positioned relative to the beam path such that the light beam propagates through the thickness of the shell and crosses the respective surface area perpendicularly, wherein the amplitude transmission factors of all surface areas are arranged within a sorted list from small values to large values, wherein the specific amplitude transmission factor is the mean value of the first 1% of the amplitude transmission factors arranged in the sorted list, the smallest one being among the first 1% of the amplitude transmission factors, wherein the average amplitude transmission factor is the mean value of all amplitude transmission factors arranged in the sorted list, wherein there is on less than 5% of the outer surface area of the shell local striae of molybdenum, platinum, iridium, tungsten, rhodium, noble metals, alloys of one or more of these materials or oxides of one or more of these materials, respectively, when the volume of the shell is projected radially outwards on the outer surface of the shell; wherein the amplitude transmission factor is the factor the amplitude of the light beam is attenuated between the light source and the detector; wherein the light beam has a wavelength of between 270 nm and 300 nm; wherein the light source comprises a laser; and wherein the outer surface of the shell is divided in 10 or more equal surface areas.

In certain illustrative embodiments, there is on less than 3% of the outer surface area of the shell said striae.

In certain illustrative embodiments, the shell has an overall average concentration of molybdenum, platinum, iridium, tungsten, rhodium, noble metals, alloys of one or more of these materials or oxides of one or more of these materials, respectively, of at least 0.1 ppm (m/m) but less than 50 ppm (m/m).

In certain illustrative embodiments, in the volume of the shell comprising the local striae the local maximal concentration of molybdenum, platinum, iridium, tungsten, rhodium, noble metals, alloys of one or more of these materials or oxides of one or more of these materials is more than 0.01% (m/m) MoO3 or less than 80% (m/m) MoO3.

In certain illustrative embodiments, in the volume of the shell comprising the local striae the local overall average concentration of molybdenum, platinum, iridium, tungsten, rhodium, noble metals, alloys of one or more of these materials or oxides of one or more of these materials is more than 0.01% (m/m) MoO3 or less than 3% (m/m) MoO3.

In certain illustrative embodiments, the specific amplitude transmission factor is smaller than or equal to 0.9999.

In certain illustrative embodiments, the ratio is greater than 1.00003.

In certain illustrative embodiments, the glass article has a length of between 1 m and 3 m.

In certain illustrative embodiments, the glass element comprises in weight percent:

| | |
|---|---|
| $SiO_2$ | 50-90 |
| $B_2O_3$ | 0-20 |

-continued

| | |
|---|---|
| $Al_2O_3$ | >0-18 |
| $Na_2O$ | 0-15 |
| $K_2O$ | 0-5 |
| $Li_2O$ | 0-2 |
| CaO | 0-15 |
| BaO | 0-6 |
| $ZrO_2$ | 0-5 |
| $TiO_2$ | 0-5 |
| $Fe_2O_3$ | 0-3 |

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
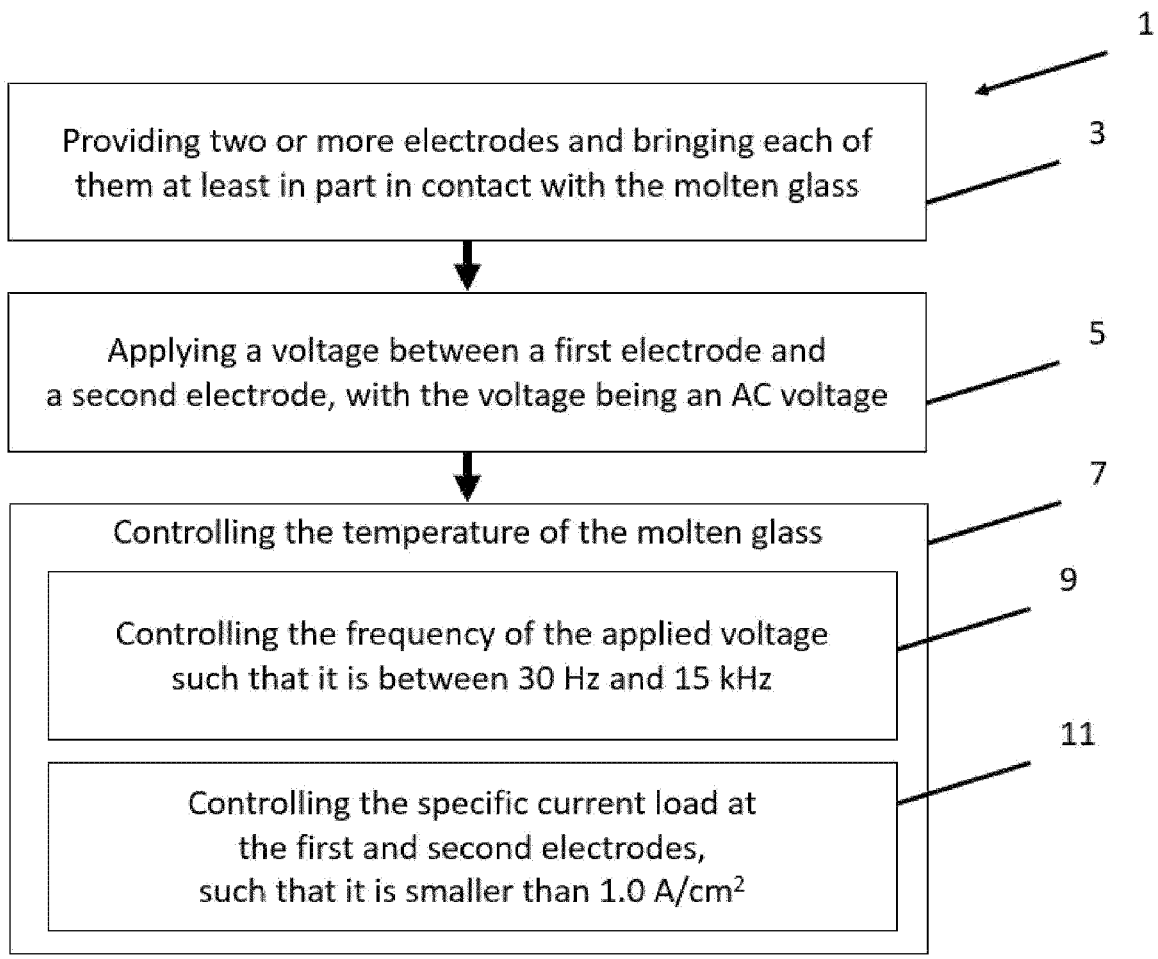
FIG. 1 shows a flow diagram of a method according to the first aspect of the disclosure.

The disclosure is, thus, based on the surprising finding that the process of how the temperature of the molten glass is controlled has a significant influence on the amount of material which is removed from the electrodes and passed over to the molten glass and on what happens with the material in the molten glass. Especially the parameters referring to the frequency and the specific current load have been identified as helpful for achieving high quality glass material.

It has been proven that applying the disclosed approach allows significantly reducing the amount of electrode material in the molten glass, thus, in the final glass products. Moreover, even if there remains electrode material of minor concentration in the molten glass, the electrode material appears to show less tendency to accumulate in the solid glass material when the disclosed approach is applied. The same applies for oxides and/or alloys of these materials.

While not bound by any theory, it is assumed that the positive effects originate from the specific heating process introduced by controlling the temperature. This is supported by the fact that only specific values of the frequency and/or of the specific current load lead to reduced contaminations such as accumulations, hence, to the high quality glass articles.

Relevant electrode material in this respect can particularly be molybdenum, platinum, iridium, tungsten, rhodium, alloys of one or more of these materials and/or oxides of one or more of these materials, and any combination thereof.

It is apparent that the present disclosure can be applied to any conventional glass melting furnace which employs heating by electrodes. This allows retrofitting any existing heating process by simply introducing a temperature control mechanism as proposed by the disclosure. This can be accomplished easily and without high costs which is very economic.

Thus, even if there are still minor amounts of electrode material present in the molten glass, it has been successfully achieved that no accumulations, hence, no striae are present any longer in the cooled glass.

The glass produced with the disclosed method allows to produce glass articles of high quality. For example, for producing glass material used in the field of pharmaceutical containers, the disclosed method may be employed. Especially for pharmaceutical containers such as vials, syringes, cartridges, ampoules and the like it is advantageous to have glass material of high quality. High quality ensures that pharmaceutical compositions held by the containers do substantially not get in contact with any contaminations.

In some embodiments, the specific current load is an average specific current load over the surface of the respective electrode which has contact with the molten glass.

In some embodiments, each electrode has a surface area but only a part of the surface area has contact with the molten glass. In some embodiments said part of the surface area is relevant for the specific current load.

In some embodiments, the specific current load at the first and/or second electrode is obtained with respect to a surface of the respective electrode which equals a fraction of ⅔ of its geometric electrode surface. In other words, the specific current load at the first and/or second electrode is obtained with respect to a surface $A_{\mathit{eff}}$ which is equal to $\frac{2}{3} * A_{geom}$, wherein $A_{geom}$ is the geometric surface of the respective electrode. In some embodiments said surface $A_{\mathit{eff}}$ is used for electrodes or pair of electrodes which are of the form of rod electrodes, especially if the electrodes do not heat tip to tip, but across. For example, an electrode in form of a cylinder of height h and radius r has a geometric surface of $A_{geom} = h*2*PI*r + 2*PI*r^2$.

In some embodiments the specific current load at the first and/or second electrode is obtained with respect to a surface of the respective electrode which equals the geometric surface $A_{geom}$ of the respective electrode, especially if the electrodes heat tip to tip and/or if the electrodes are in form of a sphere. For example, an electrode in form of a sphere of radius r has a geometric surface of $A_{geom} = 4*PI*r^2$.

In some embodiments, in case the respective electrode is or comprises a rod electrode, the specific current load is determined with respect to 66% (=⅔) of the entire contact surface of that electrode. This might be viewed as the "active" surface of the electrode in the heating scenario of a heating circuit comprising a pair of electrodes. Hence, the part of the electrode surface not facing the other one of the pair of electrodes has less weight.

In some embodiments, controlling the specific current load at the first and/or second electrode may comprise that the respective specific current load is 0.01 A/cm² or more, 0.05 A/cm² or more, 0.1 A/cm² or more, 0.2 A/cm² or more, 0.3 A/cm² or more, 0.4 A/cm² or more, 0.5 A/cm² or more, 1.0 A/cm² or more, 1.5 A/cm² or more, 2.0 A/cm² or more or 2.5 A/cm² or more at the surface of the electrode which has contact with the molten glass.

In some embodiments, controlling the specific current load at the first and/or second electrode may comprise: Controlling the specific current load at the first and/or second electrode, such that it is 2.5 A/cm² or less, 2.0 A/cm² or less, 1.5 A/cm² or less, 1.0 A/cm² or less, 0.5 A/cm² or less, or 0.3 A/cm² or less at the surface of the electrode which has contact with the molten glass.

In some embodiments, controlling the specific current load at the first and/or second electrode may comprise that the specific current load at the first electrode and the specific current load at the second electrode are different. Especially there is a first specific current load at the first electrode and a second specific current load, which is different compared to the first specific current load, which especially is higher or lower, at the second electrode. For each of the specific current load, such as the first specific current load and the second specific current load, one or more limits of the specific current load as stated above may be chosen, especially an upper limit and/or a lower limit.

For example, the current load at the first electrode may be controlled such that it is 2.0 A/cm² or less while the current load at the second electrode may be controlled such that it is 0.5 A/cm² or less. This means, each specific current load here has an upper limit.

For example, the current load at the first electrode may be controlled such that it is 2.0 A/cm² or less and 0.5 A/cm² or more while the current load at the second electrode may be controlled such that it is 0.5 A/cm² or less and 0.1 A/cm² or more. This means, each specific current load here has an upper limit and a lower limit.

In some embodiments there are two or more pairs of first and second electrodes employed. In this situation the frequency of the voltage applied between each pair and/or the specific current load at each of the further first and/or second electrode may be controlled individually, likewise as described herein, especially as described above with respect to the first and second electrodes.

A very flexible setup is possible, if two or more pairs of electrodes, in some embodiments, pairs of first and second electrodes are used within the method. Since the electrodes of all pairs of electrodes may contribute to the contamination of the glass, in some embodiments some or even all electrodes are operated according to the disclosure.

In some embodiments of the method, one or more third electrodes or one or more pairs of third electrodes are provided and the method further comprises: Bringing each of them at least in part in contact with the molten glass. The method then may further comprise: Applying a voltage between the first electrode, the second electrode, one, two or more of the third electrodes, or any combination of these electrodes, with the voltage being an AC voltage. The frequency and/or the specific current load with respect to these third electrodes may then be controlled likewise as it has been described herein with respect to the first and second electrodes.

In some embodiments the frequency and/or the specific current load may be controlled individually for one or more or even all of the third electrodes.

In some embodiments, different pairs of electrodes might be operated with different specific current loads, especially with different first and second specific current loads.

In some embodiments, different pairs of electrodes might be operated with different frequencies. For example there might be at least two pairs of electrodes, such as two pairs of first and second electrodes. One pair might then be operated with a first frequency, such as 50 Hz, and another pair might then be operated with a second frequency, such as 10 kHz.

In some embodiments there are 2 or more, 5 or more, 10 or more, 15 or more, 20 or more, 25 or more, 30 or more, 35 or more, 40 or more, or 50 or more pairs of electrodes. In some embodiments there are 100 or less, 80 or less, 50 or less, 40 or less, 30 or less, 20 or less or 10 or less pairs of electrodes.

In some embodiments there might be in total 2 or more, 5 or more, 10 or more, 15 or more, 20 or more, 25 or more, 30 or more, 35 or more, 40 or more, 45 or more, 50 or more, 55 or more, 60 or more, 70 or more, 80 or more, 90 or more, or 100 or more electrodes, such as first, second and/or third electrodes. In some embodiments there are 200 or less, 100 or less, 80 or less, 50 or less, 40 or less, 30 or less, 20 or less or 10 or less of electrodes.

If there are provided a plurality of electrodes, and in some embodiments if the electrodes are at least in part be controlled individually, a highly precise heating procedure can be provided. This allows that glass material of particular high quality can be obtained.

It might be, of course, also possible in some embodiments that the frequency and/or the specific current load is/are controlled for some one or all of the electrodes individually, in line with the ranges provided herein for the frequency and the specific current load.

In some embodiments, one or more, such as all, of the electrodes may belong to the same heating circuit, such as in a heating apparatus for heating molten glass.

In some embodiments, all or some of the electrodes may have different effective areas.

The electrodes may be arranged in one single melting area or may be distributed across two or more different melting areas, which in some embodiments are separated from each other.

In some embodiments the first electrode is a rod electrode and/or the second electrode is part of a segment of a wall, which wall in some embodiments defines at least in part a volume for holding the molten glass, wherein in some embodiments the molten glass contacts at least parts of the wall while applying a voltage between the first and second electrodes.

A rod electrode provides a high degree of freedom to be arranged in the glass melting furnace. If an electrode is designed as part of a segment of the wall, the electrodes can be provided within a compact setup.

In some embodiments controlling the frequency of the applied voltage comprises controlling the frequency of the applied voltage such that it is between 30 Hz and 100 Hz or between 1 kHz and 11 kHz, such as between 9 kHz and 11 kHz; and/or controlling the specific current load at the first and/or second electrode comprises controlling the specific current load at the first and/or second electrode, such that it is 1.0 A/cm$^2$ or less, such as 0.5 A/cm$^2$ or less, such as 0.3 A/cm$^2$ or less.

Controlling the specific current load at the first and/or second electrode comprises controlling the specific current load at the first and/or second electrode, such that it is 1.0 A/cm$^2$ or less, such as 0.5 A/cm$^2$ or less, such as 0.3 A/cm$^2$ or less.

It has been proven to be beneficial that the frequency and the specific current load is chosen based on the specific situation and the respective step carried out in the process of preparing the glass material. For example if the molten glass is heated during the late process step of refining the molten glass, lower specific current loads might lead to better results. Otherwise, for process steps carried out before the refining, a higher specific current load might be provided.

Without being bound to any theory, it is assumed that one reason for this is that reduced specific current loads allow to "destroy" accumulation of contaminations.

In some embodiments controlling the frequency of the applied voltage comprises controlling the frequency of the applied voltage such that it is between 30 Hz and 100 Hz and/or controlling the specific current load at the first and/or second electrode comprises controlling the specific current load at the first and/or second electrode, such that it is 0.5 A/cm$^2$ or less, such as 0.3 A/cm$^2$ or less.

In some embodiments controlling the frequency of the applied voltage comprises controlling the frequency of the applied voltage such that it is between 1 kHz and 15 kHz, such as between 9 kHz and 15 kHz, such as between 9 kHz and 11 kHz, such as 10 kHz, and/or controlling the specific current load at the first and/or second electrode comprises controlling the specific current load at the first and/or second electrode, such that it is 2.5 A/cm$^2$ or less, such as 2.0 A/cm$^2$ or less, 1.5 A/cm$^2$ or less, or 1.0 A/cm$^2$ or less.

Hence, in some embodiments for a reduced frequency, such as 50 Hz, the specific current load is reduced, such as less than 0.5 A/cm$^2$. This way the corrosion of the electrode can be significantly reduced. Likewise, for higher frequencies, say 10 kHz, a higher specific current load might be chosen, say less than 1.0 A/cm$^2$.

In some embodiments the first and/or second electrodes comprise(s) molybdenum, tungsten, noble metals and/or one of the following alloys: (i) >95 weight % of Mo, (ii) >95 weight % of W, (iii) 80-100 weight % of Pt, 5-20 weight % of Rh, 0-10 weight % of Ir and 0-10 weight % of Au, and/or (iv) >95 weight % of Ir; and/or that the first and/or second electrodes comprise(s) at least area by area an oxide layer which provides an outer surface area of the electrode, especially when the respective electrode comprises molybdenum and/or tungsten, wherein in some embodiments the oxide layer comprises molybdenum oxide and/or tungsten oxide.

Electrodes comprising these materials have been proven well-suited for the process of melting and heating glass. If the electrode comprises an oxide layer it is more robust against the glass material, especially in case of aggressive glass materials.

In some embodiments controlling the temperature of the molten glass comprises (a) controlling that the frequency is between 9 kHz and 11 kHz and that the specific current load is 2 A/cm$^2$ or less or 1 A/cm$^2$ or less and/or (b) controlling that the frequency is between 45 Hz and 55 Hz and that the specific current load is 0.5 A/cm$^2$ or less or 0.2 A/cm$^2$ or less.

In some embodiments these limiting values are valid for an arbitrary arrangement and/or an arbitrary number of electrodes in a melter.

Said limiting values can be chosen because this way contaminations such as material of the electrodes can significantly be reduced or even avoided.

Carrying out the method with the respective combination of values for the frequency and the specific current load leads to particularly beneficial results. Here, the contaminations are greatly reduced.

In some embodiments the voltage between the first and second electrodes has an amplitude of between 10 and 600 V, which is in some embodiments chosen based on the glass material, such as based on the alkaline content of the glass material, and/or that the voltage is chosen such that the current flow between the first and second electrodes has an amplitude of between 50 and 2000 A, such as of between 50 and 500 A.

Choosing the value of the voltage within the mentioned range leads to particularly improved glass materials. It has been found that the voltage value is a particularly sensitive parameter in dependence on the alkaline content of the glass material. For example for products in the pharmaceutical field, typical alkaline contents may range from 3-10%.

Ensuring a respective current flow load leads to particularly beneficial results. Here, the contaminations are greatly reduced.

In some embodiments bringing each of the electrodes in contact with the molten glass comprises inserting at least one of the electrodes, such as the first electrode, into the molten glass at least in part, and/or that bringing each of the electrodes in contact with the molten glass comprises filling the molten glass around at least a part of at least one of the electrodes, such as the second electrode.

Inserting the electrodes allows incorporation of moveable electrodes, e.g. first filling the glass material in the respective volume for holding the molten glass and then inserting the electrodes.

Filling the molten glass around the electrodes allows incorporation of fixed electrodes, e.g. filling the glass material (partially) around them while the electrodes are arranged at least in part within the volume for holding the molten glass.

In some embodiments the method further comprises the step of: controlling the duration that at least one of the electrodes has contact with the molten glass and/or separating at least one of the electrodes from contact with the molten glass after 144 hours, such as after 48 hours, after they got in contact with the molten glass.

A precise control of the heating duration allows to achieve particular desired glass material.

In some embodiments controlling the duration, the voltage, the frequency and/or the specific current load leads to an amount of the material of the first and/or second electrode in the molten glass of at least 0.1 ppm, such as of at least 0.5 ppm, but less than 50 ppm, such as less than 30 ppm, such as less than 20 ppm, even such as less than 10 ppm, and such as less than 5 ppm, respectively, with respect to the weight amount of molten glass.

It is highly appreciated that the amount of electrode material can be reduced significantly by the proposed approach.

In some embodiments the molten glass comprises
0-1% by weight, such as 0-0.3%, 0-500 ppm, of $As_2O_3$,
0-1% by weight, such as 0-0.3%, 0-1000 ppm, of $Sb_2O_3$ and/or
0-1% by weight, such as 0-0.5%, 0-2500 ppm, of $SnO_2$, respectively, as refining agent.

A respective refining agent has been proven to be advantageous for obtaining glass material of improved quality in the context of the present disclosure.

A value of between 2% by weight and 3% by weight of $Fe_2O_3$ as redox buffer can be provided for production of brown glass.

A value of between 100 ppm and 800 ppm, such as of between 200 and 600 ppm, such as of between 400 ppm and 500 ppm, such as of 450 ppm, of $As_2O_3$ as refining agent can be provided.

In some embodiments the molten glass comprises more than 0.03% by weight and less than 1% by weight, such as 0.03-0.5%, 0.03-0.3%, 0.03-0.2%, of one halide, such as NaCl, KCl, $CaCl_2$, $MgCl_2$, $BaCl_2$, $SrCl_2$ or Z, as refining agent.

A respective refining agent has been proven to be advantageous for obtaining glass material of improved quality in the context of the present disclosure.

Of course, even if one type of halide is present in a possible concentration, it is nevertheless possible that there are one or more other types of halides present as well (be it in a one concentration or in some other one). I.e. it is not the exclusive presence of one single halide only required.

For example typical Cl contents may be from 0.05 to 0.5 weight-% in glass, such as in case of chloride refining.

In some embodiments the molten glass comprises between 20 ppm and 500 ppm (m/m) or between 2% by weight and 3% by weight, respectively, of $Fe_2O_3$ as redox buffer against an oxygen reboil.

A respective redox buffer has been proven to be advantageous for obtaining glass material of improved quality in the context of the present disclosure.

It is the astonishing finding that a glass article of particularly high quality is obtained if the respective specific and average amplitude transmission factors are chosen appropriately so as to obtain a respective ratio. It is assumed that the two factors are sensitive to the structure and local chemical composition of the glass article. Hence, a certain ratio corresponds to certain glass articles.

With the proposed method it is possible to provide glass material which is of high quality and which allows to produce glass articles with said transmission factors. The glass article may be in some embodiments directed to a pharmaceutical container. For example the glass article may be a vial, syringe, cartridge, ampoule and the like. Appropriate transmission factors, hence a respective ratio, allow to provide high quality that ensures that pharmaceutical compositions held by the containers do substantially not get in contact with any contaminations.

The relevant (electrode) materials which may cause contaminations might in some embodiments be molybdenum, platinum, iridium, tungsten, rhodium, noble metals, alloys of one or more of these materials and/or oxides of one or more of these materials.

The light transmission analysis can be carried out in a particularly convenient manner if the glass article is divided into multiple parts. This way it is easily possible to route the light beam through the shell thickness in a manner that the beam leaves the material of the glass article perpendicular to the respective surface area.

This means that each part of the multiple parts can for example be analyzed successively, one after the other.

The light beam may have a circular cross section in a plane perpendicular to the beam path. The size of the individual surface areas may be chosen such, that the complete cross-sectional area of the light beam can be arranged within a single surface area.

This allows obtaining a stable measurement result because the light beam probes only one single surface area at the same time.

Thus, in some embodiments, the surface areas are chosen such that the cross-sectional area of the light beam can be arranged within a single surface area. In some embodiments the surface area might be chosen to be of curved rectangular shape. In some embodiments they might be chosen such that the cross-sectional area of the light beam touches two, three or four edges of a surface area during the measurements. In some embodiments the light beam propagates through one single surface area at the same time.

It is acknowledged that the light beam, or to be more precise, its cross-section, does not have to cover the entire individual surface area. It turned out that the measurement results are still reliable, if the cross-sectional area of the light beam is only a fraction of the area of the surface area.

In some embodiments the cross-sectional area of the light beam in the plane of a surface area is less than 90%, such as less than 80%, less than 70%, less than 60% or less than 50%, of the surface area itself. In some embodiments the cross-sectional area of the light beam in the plane of a surface area is more than 10%, such as more than 20%, more than 40%, more than 50%, or more than 60%, of the surface area itself.

In some embodiments the extension of the surface area is chosen in both directions such that the outer surface can be divided into an integer number of surface areas. Hence, the individual surface areas may have different extensions in a first and second direction, i.e. the length of the two edges might be different. Of course, since the surface of the glass article is at least partly curved, also the surface area along with its edges might be curved.

If the wavelength of the light beam, such as of a laser, is in the chosen range, the light transmission analysis of the glass article is particularly sensitive to molybdenum, which has an absorption maximum within this range. Of course, other electrode materials might be detected as well. Hence, a glass article having a respective ratio has less accumulation of molybdenum.

A laser is a cheap and easy to use way that allows conducting the proposed measurements.

If the amplitude transmission factors of the surface areas are individually corrected so as to be independent from the distance, the light beam propagates for the respective pixel through the glass material of the glass article, different material thicknesses of the glass article may be taken into consideration.

For example such a normalization might be carried out in that internally for each amplitude transmission factor (say T), the amplitude absorption factor (such as $A=1-T$) is determined. The amplitude absorption factor is then corrected based on the distance, the light beam propagates for the respective pixel through the glass material of the glass article. Based on the corrected amplitude absorption factor the corrected amplitude transmission factor can easily be obtained. The corrected amplitude transmission factor is then used throughout the light transmission analysis.

An exemplary way to carry out such a normalization might incorporate appropriate phase measurements of the light beam at the different pixels. For example, if the individual distance the light beam propagates in the glass material is Y for an individual pixel and the maximal distance the light beam propagates in the glass material which has been determined across all pixels is Z, then a correction of the amplitude absorption factor might be obtained as follows: $A_{corrected}=(1-T)\times Z/Y$ and $T_{corrected}=1-A_{corrected}$.

In some embodiments, dividing the glass article into two or more parts means physically dividing, such as cutting or sawing, the glass article into two or more parts.

In some embodiments, the specific amplitude transmission factor is smaller than or equal to $(1-Z/100)$, wherein Z is twice the value of the detection threshold.

In some embodiments the thickness of the shell is 0.01 cm or more, 0.03 cm or more, 0.05 cm or more, 0.1 cm or more, 0.3 cm or more, 0.5 cm or more, 1 cm or more, 2 cm or more, 3 cm or more, 5 cm or more or 10 cm or more. In some embodiments the thickness of the shell is 10 cm or less, 5 cm or less, 3 cm or less, 2 cm or less, 1 cm or less, 0.5 cm or less, 0.3 cm or less, 0.1 cm or less, 0.08 cm or less, 0.05 cm or less or 0.03 cm or less.

In some embodiments the thickness of the shell is between 0.01 cm and 2 cm, such as between 0.03 and 1.5 cm, such as between 0.03 cm and 1 cm.

In some embodiments the length of the glass article is 1 cm or more, 3 cm or more, 5 cm or more, 10 cm or more, 50 cm or more, 100 cm or more or 150 cm or more In some embodiments the length of the glass article is 2 m or less, 1.5 m or less, 1 m or less, 50 cm or less, 30 cm or less, 10 cm or less, 5 cm or less or 3 cm or less.

In some embodiments the glass material of the glass article comprises soda-lime glass, borosilicate glass, alkaline-resistant glass and/or aluminosilicate glass. Optionally, a borosilicate glass is used.

Dependent on the one or more relevant materials which causes contamination of the glass article, it might be advantageous to choose the wavelength used in the light transmission analysis appropriate.

In some embodiments, two or more light transmission analysis of the glass article are carried out, each with a different wavelength of the light beam, wherein in some embodiments for each analysis the ratio of the respective average amplitude transmission factor and the respective specific amplitude transmission factor is greater than 1.00001.

This way, for each one of the different materials (which are causing at least in part the contamination of the glass article), an average amplitude transmission factor and a specific amplitude transmission factor are obtained, hence, a ratio of said factors is obtained. Optional for each material an individual amplitude transmission factor and/or an individual specific amplitude transmission factor apply. Further optional for each material an individual ratio might apply.

In other words, in some embodiments the one or more light transmission analysis of the glass article are carried out with appropriate wavelengths of the light beam dependent on the (electrode) material which causes contamination of the glass article. The wavelength can be chosen such that it is sensitive for a specific contamination in the glass article. For example, the wavelength might be chosen in line of absorption maxima of the respective material representing the contamination.

In some embodiments the specific amplitude transmission factor is smaller than or equal to 0.99999, smaller than or equal to 0.9999, smaller than or equal to 0.999, smaller than or equal to 0.99, is between 0.98 and 0.99999, such as between 0.985 and 0.9999, such as between 0.99 and 0.9999 or between 0.985 and 0.999. Optional the specific amplitude transmission factor is larger than 0.8, larger than 0.9, larger than 0.95 or larger than 0.99.

In some embodiments the average amplitude transmission factor is larger than or equal to 0.95, larger than or equal to 0.98, larger than or equal to 0.99, larger than or equal to 0.995, larger than or equal to 0.997, larger than or equal to 0.999, is between 0.95 and 1, such as between 0.96 and 1, such as between 0.98 and 1, such as between 0.99 and 1, such as between 0.99 and 0.99999. Optional the average amplitude transmission factor is smaller than 0.99999, smaller than 0.99995 or smaller than 0.9999.

In some embodiments the ratio is greater than 1.00002, greater than 1.00005, greater than 1.0001, greater than 1.00015, greater than 1.0003, greater than 1.0005, greater than 1.001, greater than 1.005 or greater than 1.01. Optional the ratio is smaller than 1.2, smaller than 1.1, smaller than 1.01 or smaller than 1.001.

In some embodiments dependent on the (electrode) material which causes contamination of the glass article and/or dependent on the wavelength used for the analysis an individual range for the specific amplitude transmission factor applies.

In some embodiments dependent on the (electrode) material which causes contamination of the glass article and/or dependent on the wavelength used for the analysis an individual range for the average amplitude transmission factor applies.

In some embodiments dependent on the (electrode) material which causes contamination of the glass article and/or dependent on the wavelength used for the analysis an individual range for the ratio applies.

This means that for all analysis the same factors and/or ratios apply or that at least for some or all analysis some factors and/or the ratio is chosen individually.

In the following table for each of different materials, including alloys and oxides, which might cause contaminations of the glass article two suitable ranges of wavelengths for the light transmission analysis are provided. For example, dependent on the material causing the contamination, a respective wavelength might be chosen from the table.

In some embodiments, for each of the one or more light transmission analysis of the glass article, a certain wavelength of one of the ranges provided in the table might be chosen.

| Material | Range of Wavelengths [nm] | Suitable range of Wavelengths [nm] |
| --- | --- | --- |
| Molybdenum or an alloy thereof and/or a molybdenum oxide | 270-300 | 275-290 |
| Platinum or an alloy thereof and/or a platinum oxide | 280-440 | 360-370 |
| Iridium or an alloy thereof and/or an iridium oxide | 500-650 | 500-550 |
| Tungsten or an alloy thereof and/or a tungsten oxide | 250-350 | 300-350 |
| Rhodium or an alloy thereof and/or a rhodium oxide | 350-520 | 450-490 |

For example, one or more wavelengths for a respective number of analysis might be chosen for the light beam from the group consisting of: 275 nm, 365 nm, 520 nm, 320 nm and 420 nm. For example two, three, four or five wavelengths might be chosen. For example, for two analysis, one analysis might be carried out with a wavelength of 275 nm and another analysis might be carried out with a wavelength of 365 nm. This allows to incorporate contaminations due to molybdenum oxide and platinum oxide.

It is noted that for contaminations of the glass article due to oxides, the selection of a material-specific wavelengths as provided in the table can be provided. In case the contaminations are for example due to particles of metal, the transmission of light might be affected over a broader portion of the spectrum, so that the analysis is more robust with respect to the choice of the wavelength.

In some embodiments one or more, in some embodiments at least in part different, wavelengths for a respective number of analysis are chosen from the range 250 nm to 800 nm. This can particularly be provided in case of pure metal contaminations.

In case two or more light transmission analysis of the glass article are carried out, in some embodiments the analysis are carried out either in parallel or in sequence. Using more than one beam paths, in some embodiments along with a respective number of detectors, the analysis with two or more wavelengths can be carried out in parallel. This is fast.

If for example contaminations in the glass article are originating from molybdenum and tungsten, two light transmission analysis of the glass article might be carried out. A first one with a wavelength sensitive for molybdenum (e.g. 285 nm) and a second one with a wavelength sensitive for tungsten (e.g. 320 nm). This way two ratios are obtained for each of the materials.

In some embodiments the shell has an overall average concentration of molybdenum, platinum, iridium, tungsten, rhodium, noble metals, alloys of one or more of these materials and/or oxides of one or more of these materials, respectively, of at least 0.1 ppm (m/m) but less than 50 ppm (m/m), such as less than 30 ppm (m/m), such as less than 20 ppm (m/m), even such as less than 10 ppm (m/m), such as less than 5 ppm (m/m); and/or wherein the shell has local striae of molybdenum, platinum, iridium, tungsten, rhodium, noble metals, alloys of one or more of these materials and/or oxides of one or more of these materials, respectively, on less than 5%, such as on less than 3%, such as on less than 1%, such as on less than 0.5%, such as on less than 0.1%, such as on less than 0.01%, such as on less than 0.003% and such as on less than 0.001%, of the outer surface area of the shell, when the volume of the shell is projected radially outwards on the outer surface of the shell, and/or wherein in the volume of the glass article, such as in the shell, comprising the local striae the local maximal concentration of molybdenum, platinum, iridium, tungsten, rhodium, noble metals, alloys of one or more of these materials and/or oxides of one or more of these materials is more than 0.01% (m/m) $MoO_3$ and/or less than 80% (m/m) $MoO_3$, and/or the local overall average concentration of molybdenum, platinum, iridium, tungsten, rhodium, noble metals, alloys of one or more of these materials and/or oxides of one or more of these materials is more than 0.01% (m/m) $MoO_3$ and/or less than 3% (m/m) $MoO_3$.

The disclosed overall average concentration of the respective materials allows to control the quality of the glass article in an easy and particularly precise manner.

In some embodiments, the shell has an overall average concentration of molybdenum of at least 0.1 ppm (m/m), such as of at least 0.5 ppm (m/m), such as of at least 0.9 ppm (m/m), such as of more than 1 ppm (m/m).

In some embodiments, the shell has an overall average concentration of molybdenum and further electrode materials of at least 0.1 ppm (m/m), such as of at least 0.5 ppm (m/m), such as of at least 0.9 ppm (m/m), such as of more than 1 ppm (m/m).

In some embodiments, the shell has an overall average concentration of molybdenum of between 0.9 and 1.8 ppm (m/m), such as of between 1.1 and 1.5 ppm (m/m).

In some embodiments, the shell has an overall average concentration of molybdenum of less than 50 ppm (m/m), such as less than 30 ppm (m/m), such as less than 20 ppm (m/m), such as less than 10 ppm (m/m), such as less than 5 ppm (m/m).

Glass articles which have striae of only limited relative coverage are of particular interest because only less or even no unwanted materials are present. This improves quality to a great extent.

If any accumulations of respective materials are limited with respect to both, the maximal and average concentration, it is possible to obtain glass articles of good quality.

In some embodiments the glass article has a maximal extension and/or length of between 1 m and 3 m, such as of between 1 m and 2 m, and/or of between 1 and 1000 times of the outer diameter of the shell, such as of between 10 and 100 times of the outer diameter of the shell.

In some embodiments the glass article comprises in weight percent

| | |
|---|---|
| $SiO_2$ | 50-90 |
| $B_2O_3$ | 0-20 |
| $Al_2O_3$ | >0-18 |
| $Na_2O$ | 0-15 |
| $K_2O$ | 0-5 |
| $Li_2O$ | 0-2 |
| CaO | 0-15 |
| BaO | 0-6 |
| $ZrO_2$ | 0-5 |
| $TiO_2$ | 0-5 |
| $Fe_2O_3$ | 0-3 |

A respective material of the glass article has been proven to be advantageous for obtaining a glass article of improved quality in the context of the present disclosure.

Referring now to the drawings, FIG. 1 shows a flow diagram of a method 1 for heating molten glass according to the first aspect of the disclosure. The method 1 comprises different steps.

Step 3 is directed to providing two or more electrodes and bringing each of them at least in part in contact with the molten glass.

The first electrode is a rod electrode and the second electrode is part of a segment of a wall, which wall defines at least in part a volume for holding the molten glass, wherein the molten glass contacts the wall while applying a voltage between the first and second electrodes.

The first and second electrodes comprise molybdenum. The first and second electrodes comprise at least area by area an oxide layer which provides an outer surface area of the electrode.

Bringing each of the electrodes in contact with the molten glass comprises inserting the first electrode into the molten glass at least in part and filling the molten glass around at least some part of the second electrode.

Step 5 is directed to applying a voltage between a first electrode and a second electrode, with the voltage being an AC voltage.

Step 7 is directed to controlling the temperature of the molten glass.

The step 7 comprises step 9 directed to controlling the frequency of the applied voltage such that it is between 30 Hz and 15 kHz.

The step 7 also comprises step 11 directed to controlling the specific current load at the first and second electrodes, such that it is smaller than 1.0 A/cm$^2$ at the surface of the electrode which has contact with the molten glass.

For example, in step 7 the frequency might be chosen such that it is between 30 Hz and 100 Hz and the specific current load might be chosen such that it is less than 0.5 A/cm$^2$.

For example, in step 7 the frequency might also be chosen such that it is between 1 kHz and 15 kHz and the specific current load might be chosen such that it is less than 1.0 A/cm$^2$.

Figure 2:
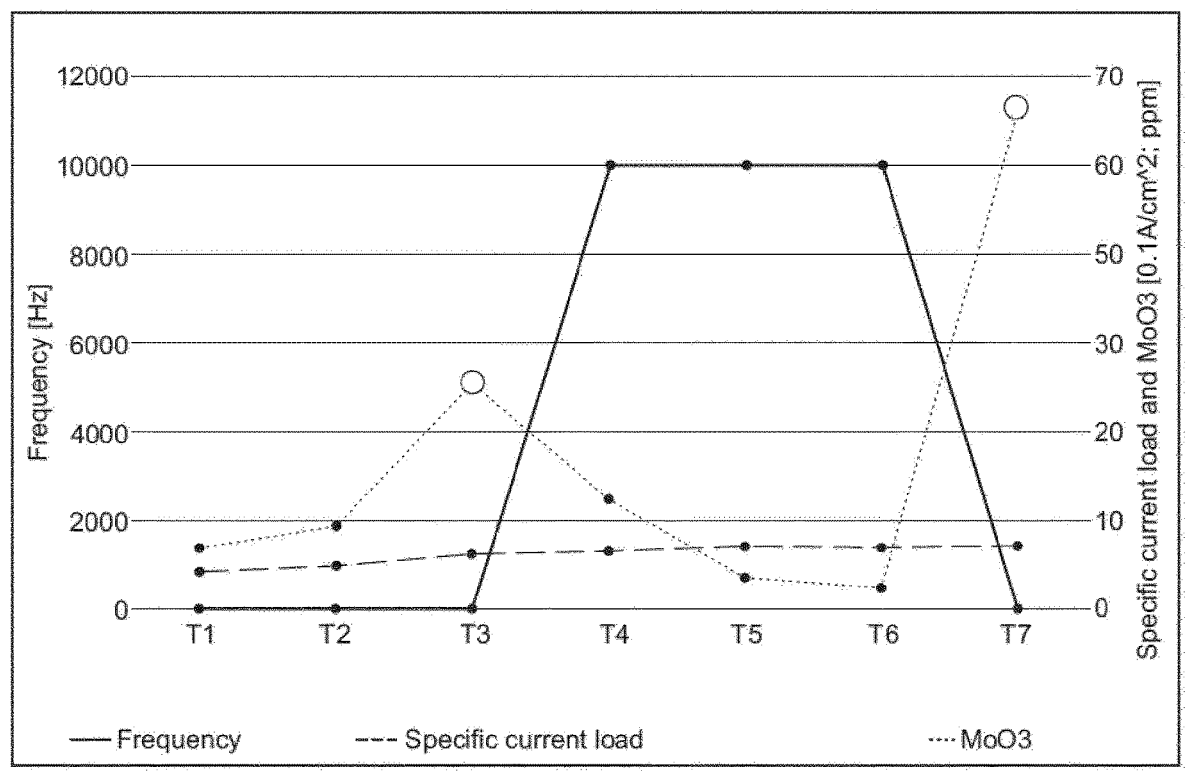
FIG. 2 shows a diagram indicating the amount of Mo in the solid glass material dependent on the frequency of the applied voltage and the specific current load.

FIG. 2 shows a diagram indicating the amount of Mo in the solid glass material dependent on the frequency of the applied voltage and the specific current load.

In the diagram a first curve (solid line) represents the frequency of the applied voltage. The frequency is changed at some instance of time (T3→T4) from 50 Hz to 10000 Hz and to a later instance of time (T6→T7) back to 50 Hz.

In the diagram a second curve (dashed line) represents the specific current load of less than 1.0 A/cm$^2$, which is more precisely about between 0.6 and 0.8 A/cm$^2$.

In the diagram a third curve (dotted line) represents the amount of Mo in the produced solid glass material.

The diagram indicates on the left vertical axis the value of the frequency for the applied voltage in Hz. The diagram indicates on the right vertical axis the value of the specific current load and the amount of Mo, in 0.1 A/cm$^2$ and ppm, respectively.

It is apparent that the amount of Mo is strongly dependent on the frequency of the applied voltage and the specific current load at the electrodes.

For a frequency of 10 kHz apparently no particles are present, such as for specific current loads of less than 1 A/cm$^2$ or independent from the specific current load.

It turned out that for frequencies of 50 Hz a specific current load of less than 0.5 A/cm$^2$ is suitable. And for frequencies of 10 kHz a specific current load of less than 1 A/cm$^2$ is suitable, however, also more than 1 A/cm$^2$ might be possible in further embodiments.

A major difference between choosing a frequency of 50 Hz and 10 kHz may be that the creation of particles starts at a higher specific current load for 10 kHz than for 50 Hz. For example, the specific current load may be at least 60-100% higher for 10 kHz than for 50 Hz until creation of particles starts. Therefore, choosing a higher frequency may be suitable for preventing accumulations, i.e. particles, at least for the given current load.

Figure 3:
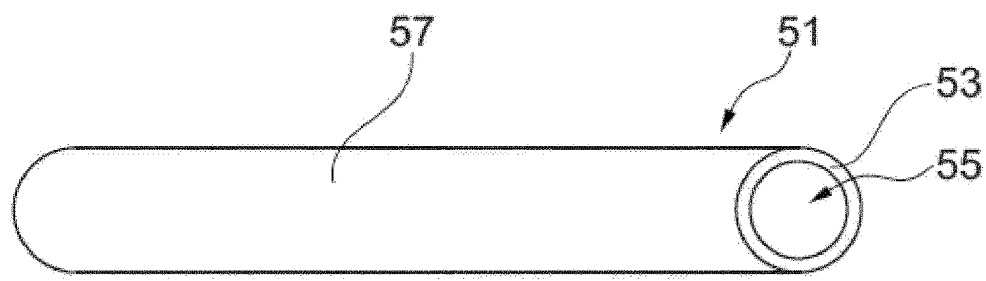
FIG. 3 shows a glass article according to the second aspect of the disclosure.

FIG. 3 shows a glass article 51 provided according to the second aspect of the disclosure. The glass article 51, which is designed in form of a glass tube element, comprises a shell 53 which encloses a lumen 55. The shell has an outer surface 57.

For a light transmission analysis of the glass article 51, the ratio of an average amplitude transmission factor and a specific amplitude transmission factor is greater than 1.00001. Here, the contamination of the glass material which is to be analyzed might be molybdenum.

Figure 4:
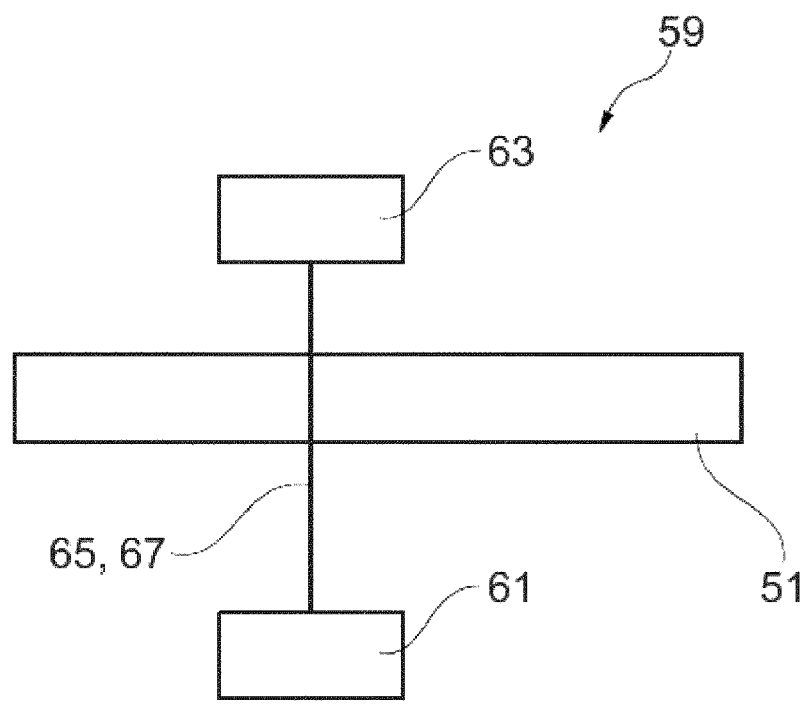
FIG. 4 shows a setup for a light transmission analysis of a glass article according to the second aspect of the disclosure in a cross-sectional view.

FIG. 4 shows a setup 59 for a light transmission analysis of a glass article such as the glass article 51 provided according to the second aspect of the disclosure in a cross-sectional view.

The setup 59 comprises a fixed light source 61 and a fixed detector 63. A light beam 65 is emitted from the light source 61 towards the detector 63 along a beam path 67. The setup 59 allows to determine an amplitude transmission factor of the light beam 65. The amplitude transmission factor is the factor, the amplitude of the light beam 65 is attenuated between the light source 61 and the detector 63.

Figure 5:
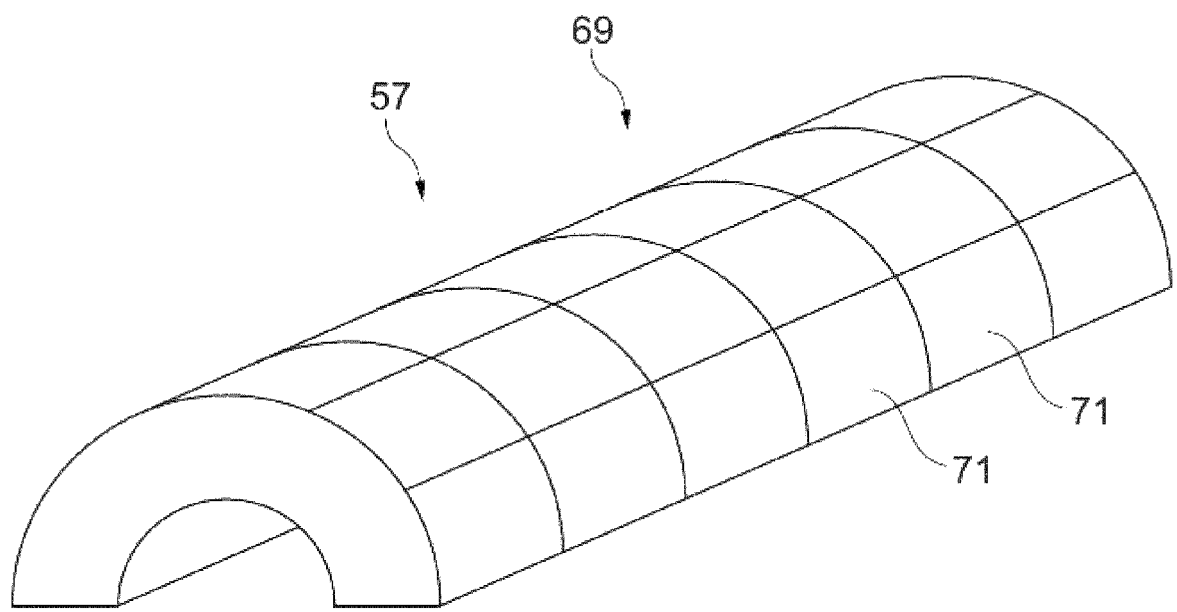
FIG. 5 shows a perspective view of a half of the glass article as used in the light transmission analysis.

The glass article 51 is divided into two halves for conducting the measurements. FIG. 5 shows one half 69 of the glass article 51 in a perspective view. The outer surface 57 of the half 69 is divided into surface areas 71 of equal shape and size. Likewise, also the other half is divided into surface areas of equal shape and size.

For every surface area 71 (of both halves of the glass article 51), the glass article 51 (or the respective half thereof) is positioned relative to the beam path 67 such that the light beam 65 propagates through the thickness of the shell 53 and crosses the respective surface area 71 perpendicularly.

It is more convenient for this measurement to have the glass article 51 divided into two halves. This allows to route the light beam 65 more easily and more accurate through the glass article 51.

Figure 6:
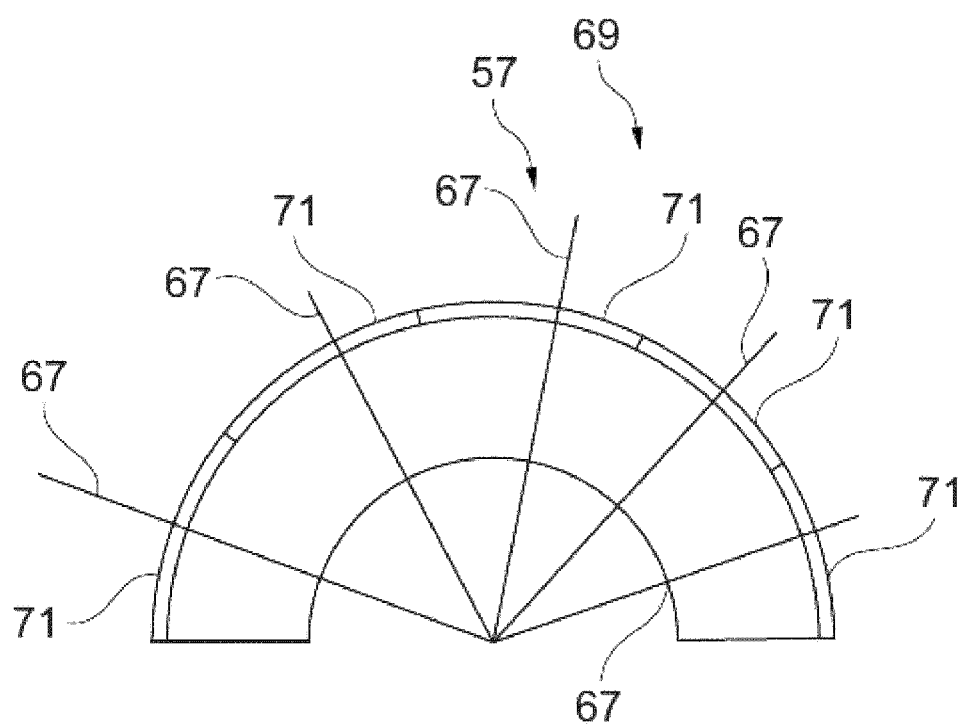
FIG. 6 shows a front view of the half of the glass article along with different beam paths.

FIG. 6 shows the half 69 of the glass article 51 in a front view. The surface areas 71 close to the front are indicated. Furthermore, different relative beam paths 67 are shown. Each of the beam paths 67 is perpendicular on the respective surface area 71.

Of course, FIG. 6 is only for illustration purposes. Typically, there is only one single beam path 67 and the glass article, or its half 57, is orientated appropriately so as to meet the measurement conditions with respect to perpendicularity of the light beam and the surface area for each single surface area. I.e. for each measurement the orientation of the glass article is adjusted. In the setup 59, the light source 61 and the detector 63 are on different sides of the glass article 51. But more than one beam paths are possible as well.

Furthermore, the surface areas 71 in FIG. 6 seem to have a certain depth within the shell of the glass tube element. This, however, is only for illustration purposes so as to more reliably indicate the surface elements 71 in the view of FIG. 6.

The amplitude transmission factors of all surface areas (of both halves of the glass article) are arranged within a sorted list from small values to large values. The specific amplitude transmission factor is the mean value of the first 1% of the amplitude transmission factors arranged in the sorted list, the smallest one being among the first 1% of the amplitude transmission factors. The average amplitude transmission factor is the mean value of all amplitude transmission factors arranged in the sorted list.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS

1 Method
3-11 Step
51 Glass article
53 Shell
55 Lumen
57 Surface
59 Setup
61 Light Source
63 Detector
65 Light beam
67 Beam path
69 Half
71 Surface area

What is claimed is:

1. A glass article, the glass article being designed at least in part in the form of a glass tube element comprising at least one shell which encloses at least one lumen, wherein for at least one light transmission analysis of the glass article, a ratio of an average amplitude transmission factor and a specific amplitude transmission factor is greater than 1.00001, wherein for the light transmission analysis, an outer surface of the at least one shell is at least virtually divided into surface areas of equal shape and size, and an amplitude transmission factor of a light beam, which is emitted from a fixed light source towards a fixed detector along a beam path, is determined consecutively for every surface area in that the glass article and/or the surface area is positioned relative to the beam path such that the light beam propagates through a thickness of the at least one shell and crosses the respective surface area perpendicularly, wherein the amplitude transmission factors of all surface areas are arranged within a sorted list from small values to large values, wherein the specific amplitude transmission factor is the mean value of the first 1% of the amplitude transmission factors arranged in the sorted list, the smallest one being among the first 1% of the amplitude transmission factors, wherein the average amplitude transmission factor is the mean value of all amplitude transmission factors arranged in the sorted list, wherein the average amplitude transmission factor is larger than or equal to 0.99;

wherein the amplitude transmission factor is the factor the amplitude of the light beam is attenuated between the light source and the detector;

wherein the light beam has a wavelength of between 270 nm and 300 nm;

wherein the light source comprises a laser; and wherein the outer surface of the at least one shell is divided in 10 or more equal surface areas, wherein the at least one shell has an overall average concentration of molybdenum, platinum, iridium, tungsten, rhodium, noble metals, alloys of one or more of these materials or oxides of one or more of these materials, respectively, of at least 0.1 ppm (m/m) but less than 50 ppm (m/m).

2. The glass article according to claim 1, wherein the average amplitude transmission factor is larger or equal to 0.993.

3. The glass article according to claim 1, wherein the specific amplitude transmission factor is smaller than or equal to 0.9999.

4. The glass article according to claim 1, wherein the ratio is greater than 1.00003.

5. The glass article according to claim 1, wherein the glass article has a length of between 1 m and 3 m.

6. The glass article according to claim 1, comprising in weight percent

| | |
|---|---|
| $SiO_2$ | 50-90 |
| $B_2O_3$ | 0-20 |
| $Al_2O_3$ | >0-18 |
| $Na_2O$ | 0-15 |
| $K_2O$ | 0-5 |
| $Li_2O$ | 0-2 |
| $CaO$ | 0-15 |
| $BaO$ | 0-6 |
| $ZrO_2$ | 0-5 |
| $TiO_2$ | 0-5 |
| $Fe_2O_3$ | 0-3. |

7. A glass article, the glass article being designed at least in part in form of a glass tube element comprising at least one shell which encloses at least one lumen, wherein for at least one light transmission analysis of the glass article, a ratio of an average amplitude transmission factor and a specific amplitude transmission factor is greater than 1.00003, wherein for the light transmission analysis, an outer surface of the at least one shell is at least virtually divided into surface areas of equal shape and size, and an amplitude transmission factor of a light beam, which is emitted from a fixed light source towards a fixed detector along a beam path, is determined consecutively for every surface area in that the glass article and/or the surface area is positioned relative to the beam path such that the light beam propagates through a thickness of the at least one shell and crosses the respective surface area perpendicularly, wherein the amplitude transmission factors of all surface areas are arranged within a sorted list from small values to large values, wherein the specific amplitude transmission factor is the mean value of the first 1% of the amplitude transmission factors arranged in the sorted list, the smallest one being among the first 1% of the amplitude transmission factors, wherein the average amplitude transmission factor is the mean value of all amplitude transmission factors arranged in the sorted list;

wherein the at least one shell has an overall average concentration of molybdenum, platinum, iridium, tungsten, rhodium, noble metals, alloys of one or more of these materials or oxides of one or more of these materials, respectively, of at least 0.1 ppm (m/m) but less than 50 ppm (m/m);

wherein the amplitude transmission factor is the factor the amplitude of the light beam is attenuated between the light source and the detector;

wherein the light beam has a wavelength of between 270 nm and 300 nm;

wherein the light source comprises a laser; and wherein the outer surface of the at least one shell is divided in 10 or more equal surface areas.

8. The glass article according to claim 7, wherein the specific amplitude transmission factor is smaller than or equal to 0.9999.

9. The glass article according to claim 7, wherein the glass article has a length of between 1 m and 3 m.

10. The glass article according to claim 7, comprising in weight percent

| | |
|---|---|
| $SiO_2$ | 50-90 |
| $B_2O_3$ | 0-20 |
| $Al_2O_3$ | >0-18 |
| $Na_2O$ | 0-15 |
| $K_2O$ | 0-5 |
| $Li_2O$ | 0-2 |
| CaO | 0-15 |
| BaO | 0-6 |
| $ZrO_2$ | 0-5 |
| $TiO_2$ | 0-5 |
| $Fe_2O_3$ | 0-3. |

11. A glass article, the glass article being designed at least in part in form of a glass tube element comprising at least one shell which encloses at least one lumen, wherein for at least one light transmission analysis of the glass article, a ratio of an average amplitude transmission factor and a specific amplitude transmission factor is greater than 1.00001, wherein for the light transmission analysis, an outer surface of the shell is at least virtually divided into surface areas of equal shape and size, and an amplitude transmission factor of a light beam, which is emitted from a fixed light source towards a fixed detector along a beam path, is determined consecutively for every surface area in that the glass article and/or the surface area is positioned relative to the beam path such that the light beam propagates through the thickness of the at least one shell and crosses the respective surface area perpendicularly, wherein the amplitude transmission factors of all surface areas are arranged within a sorted list from small values to large values, wherein the specific amplitude transmission factor is the mean value of the first 1% of the amplitude transmission factors arranged in the sorted list, the smallest one being among the first 1% of the amplitude transmission factors, wherein the average amplitude transmission factor is the mean value of all amplitude transmission factors arranged in the sorted list, wherein there is on less than 5% of an outer surface area of the at least one shell local striae of molybdenum, platinum, iridium, tungsten, rhodium, noble metals, alloys of one or more of these materials or oxides of one or more of these materials, respectively, when a volume of the at least one shell is projected radially outwards on the outer surface of the at least one shell;

wherein the amplitude transmission factor is the factor the amplitude of the light beam is attenuated between the light source and the detector;

wherein the light beam has a wavelength of between 270 nm and 300 nm;

wherein the light source comprises a laser; and wherein the outer surface of the at least one shell is divided in 10 or more equal surface areas, wherein the at least one shell has an overall average concentration of molybdenum, platinum, iridium, tungsten, rhodium, noble metals, alloys of one or more of these materials or oxides of one or more of these materials, respectively, of at least 0.1 ppm (m/m) but less than 50 ppm (m/m).

12. The glass article according to claim 11, wherein there is on less than 3% of the outer surface area of the at least one shell said striae.

13. The glass article according to claim 11, wherein in the volume of the at least one shell comprising the local striae a local maximal concentration of molybdenum, platinum, iridium, tungsten, rhodium, noble metals, alloys of one or more of these materials or oxides of one or more of these materials, respectively, is more than 0.01% (m/m) $MoO_3$ and less than 80% (m/m) $MoO_3$.

14. The glass article according to claim 11, wherein in the volume of the at least one shell comprising the local striae a local overall average concentration of molybdenum, platinum, iridium, tungsten, rhodium, noble metals, alloys of one or more of these materials or oxides of one or more of these materials, respectively, is more than 0.01% (m/m) $MoO_3$ and less than 3% (m/m) $MoO_3$.

15. The glass article according to claim 11, wherein the specific amplitude transmission factor is smaller than or equal to 0.9999.

16. The glass article according to claim 11, wherein the ratio is greater than 1.00003.

17. The glass article according to claim 11, wherein the glass article has a length of between 1 m and 3 m.

18. The glass article according to claim 11, comprising in weight percent

| | |
|---|---|
| $SiO_2$ | 50-90 |
| $B_2O_3$ | 0-20 |
| $Al_2O_3$ | >0-18 |
| $Na_2O$ | 0-15 |
| $K_2O$ | 0-5 |
| $Li_2O$ | 0-2 |
| CaO | 0-15 |
| BaO | 0-6 |
| $ZrO_2$ | 0-5 |
| $TiO_2$ | 0-5 |
| $Fe_2O_3$ | 0-3. |

* * * * *